United States Patent
Cavalie et al.

(10) Patent No.: US 11,208,515 B2
(45) Date of Patent: Dec. 28, 2021

(54) COPOLYMER HAVING THICKENING AND SUSPENSION PROPERTIES

(71) Applicant: COATEX, Genay (FR)

(72) Inventors: Herve Cavalie, Senlis (FR); Clementine Champagne, Caluire-et-Cuire (FR); Benoit Magny, Cailloux sur Fontaine (FR); Jean-Marc Suau, Lucenay (FR); Christophe Verge, Coye la Foret (FR)

(73) Assignee: COATEX, Genay (FR)

( * ) Notice: Subject to any disclaimer, the term of this patent is extended or adjusted under 35 U.S.C. 154(b) by 162 days.

(21) Appl. No.: 16/304,312

(22) PCT Filed: Jun. 2, 2017

(86) PCT No.: PCT/FR2017/051392
§ 371 (c)(1),
(2) Date: Nov. 26, 2018

(87) PCT Pub. No.: WO2017/207944
PCT Pub. Date: Dec. 7, 2017

(65) Prior Publication Data
US 2019/0135965 A1    May 9, 2019

(30) Foreign Application Priority Data
Jun. 3, 2016 (FR) .................... 16 55055

(51) Int. Cl.
*C08F 220/18* (2006.01)
*C08F 265/06* (2006.01)
*A61K 8/81* (2006.01)
*A61Q 5/02* (2006.01)
*A61Q 19/10* (2006.01)

(52) U.S. Cl.
CPC .......... *C08F 220/18* (2013.01); *A61K 8/8152* (2013.01); *A61Q 5/02* (2013.01); *A61Q 19/10* (2013.01); *C08F 265/06* (2013.01); *A61K 2800/48* (2013.01); *C08F 2800/20* (2013.01)

(58) Field of Classification Search
USPC .................. 526/320, 327; 525/303
See application file for complete search history.

(56) References Cited

U.S. PATENT DOCUMENTS

| | | | | |
|---|---|---|---|---|
| 4,133,793 A * | 1/1979 | Lewis | .............. | C08F 8/00 106/287.35 |
| 4,521,494 A * | 6/1985 | Mani | ............ | C09D 133/06 428/514 |
| 6,143,821 A * | 11/2000 | Houben | .......... | A61L 15/60 524/557 |
| 6,482,776 B1 * | 11/2002 | Matz | ............ | C04B 24/163 162/168.2 |
| 2004/0213892 A1 | 10/2004 | Jonas et al. | | |
| 2014/0112966 A1 * | 4/2014 | Souzy | ........... | C08F 220/12 424/401 |
| 2014/0179590 A1 | 6/2014 | Souzy et al. | | |
| 2015/0105527 A1 | 4/2015 | Gartner et al. | | |
| 2016/0083532 A1 | 3/2016 | Wagner et al. | | |

FOREIGN PATENT DOCUMENTS

| EP | 2 620 466 A1 | 7/2013 |
|---|---|---|
| FR | 1329008 | 4/1962 |
| FR | 3 000 085 A1 | 6/2014 |
| WO | WO 2013/072696 A1 | 5/2013 |

OTHER PUBLICATIONS

International Search Report dated Aug. 4, 2017 in PCT/FR2017/051392 filed on Jun. 2, 2017.

* cited by examiner

*Primary Examiner* — Fred M Teskin
(74) *Attorney, Agent, or Firm* — Oblon, McClelland, Maier & Neustadt, L.L.P.

(57) ABSTRACT

(EN) The invention relates to the field involved in the production of aqueous compositions comprising rheology modifying agents, in particular the production of aqueous detergent or cosmetic compositions having improved, thickening and clarity properties, as well as good suspension properties. In particular, the invention relates to a rheology modifying agent which is a copolymer obtained by means of polymerisation of at least one crosslinking monomer with at least one anionic monomer comprising at least one polymerisable ethylenic unsaturation and at least one hydrophobic non-ionic monomer comprising at least one polymerisable ethylenic unsaturation.

20 Claims, No Drawings

COPOLYMER HAVING THICKENING AND SUSPENSION PROPERTIES

The invention relates to the field of the production of aqueous compositions comprising rheology-modifying agents, in particular the production of aqueous cosmetic or detergent compositions having improved thickening and clarity properties and also good suspending properties.

In particular, the invention relates to a rheology-modifying agent which is a copolymer obtained by polymerization of at least one cross-linking monomer with at least one anionic monomer comprising at least one polymerizable ethylenic unsaturation and at least one hydrophobic nonionic monomer comprising at least one polymerizable ethylenic unsaturation.

Rheology-modifying agents, also known as thickeners or viscosity agents, are known. Generally, they are present in cleaning compositions, for example in care or personal hygiene compositions, in particular cosmetic compositions, or in homecare compositions, in particular in detergent products. These compositions are usually rich in surfactant compounds.

These agents influence the rheological properties of the formulation, in particular the viscosity and also the optical or esthetic properties such as clarity. These agents also influence the capacity to suspend or to stabilize particles within the formulation.

Among the rheology-modifying agents commonly used in aqueous formulations, mention may be made of alkali-soluble or alkali-swellable copolymers (ASE, for Alkali-Soluble Emulsion or Alkali-Swellable Emulsion, polymers). Mention may also be made of hydrophobically modified alkali-soluble or alkali-swellable copolymers (HASE, for Hydrophobically modified Alkali-Soluble Emulsion or Hydrophobically modified Alkali-Swellable Emulsion, polymers).

Aqueous compositions comprising ASE copolymers or HASE copolymers as rheology-modifying agents are also known.

For these aqueous compositions, it is sought in particular to improve their properties or their performance levels for a wide pH range. In particular, it is sought to obtain aqueous compositions having a high clarity, good properties in terms of thickening effect and also good suspending properties.

The control of the viscosity and the obtaining of aqueous compositions in the form of a continuous limpid phase are particularly sought, in particular for a wide pH range.

Thus, the properties and the performance levels of the aqueous compositions must be able to be implemented both at acid pH values and at neutral or basic pH values.

An aqueous composition has good suspending properties or a good suspending capacity when it is capable of keeping particles in suspension in its continuous phase. It must be possible for this capacity to last over time in order to obtain stable aqueous compositions, for example stable when they are stored.

Generally, the suspending properties are evaluated by applying an applicative suspension test which makes it possible to determine the value of the modulus of elasticity G', the value of Tan (δ) and the value of the elastic strength of the aqueous composition comprising a rheology-modifying agent.

In general, the particles to be suspended in the continuous phase of the aqueous composition are non-hollow or hollow solid substances. These particles to be suspended can also be liquid entities which are immiscible with the continuous phase of the aqueous composition, or else encapsulated substances or gaseous substances which can be characterized by different final shapes, textures, structures, compositions, colours and properties.

By way of indication, mention may be made of exfoliating particles, for example polyethylene particles, pounded fruit shells, pumice stones. Mention may also be made of nourishing particles, for example collagen spheres, and also pearlescent particles, for example mica titanium, glycol distearates, or else esthetic particles, for example air bubbles, flakes, pigments which are optionally coloured.

Usually, the particles to be suspended can be quite variable in size. For example, the air bubbles can have a size of 1, 2 or 3 mm.

The clarity or limpidity of the aqueous compositions can be evaluated by measuring their transmittance, generally expressed as a percentage. A composition is considered to be clear or limpid if it has a transmittance, for a wavelength of 500 nm, of at least 60%, preferably of at least 70% and even more preferentially of at least 80%.

Document FR 3000085 discloses the production of an aqueous composition for a shower gel, comprising particles in suspension in a limpid continuous phase. The cross-linking compound used is ethylene glycol dimethacrylate (EDMA) or else trimethylolpropane trimethacrylate (TMP-TMA).

Document FR 1363955 describes the production of esters of α,β-ethylenic carboxylic aliphatic monoacids and of homoperillyl alcohol.

Document US 2004 0213892 describes a polymer coated with a non-ionic nitrogenous surfactant. Document EP 2780382 discloses a polymeric latex emulsion that can be used as a thickening agent.

Document EP 2620466 relates to a method for heat treatment of particles of hydroabsorbent polymer. Document 2016 0083532 describes the preparation of particles of hydroabsorbent polymer.

The rheology-modifying agents of the prior art and the aqueous compositions of the prior art comprising them are not always satisfactory and result in problems linked to these numerous desired properties.

There is therefore a need for those skilled in the art to have available rheology-modifying agents which have improved properties, in particular properties present within aqueous compositions.

The invention makes it possible to provide a solution to all or some of the problems encountered with the rheology-modifying agents of the prior art.

Thus, the invention provides a copolymer (P1) obtained by a reaction for polymerization:
  (a) of at least one anionic monomer comprising at least one polymerizable ethylenic unsaturation; and
  (b) of at least one hydrophobic nonionic monomer comprising at least one polymerizable ethylenic unsaturation; and
  (c) of at least one monomer of formula (I):

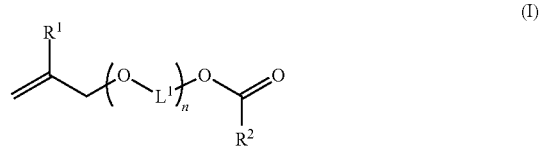

wherein:
  $R^1$ independently represents H or $CH_3$;

$R^2$ independently represents
—(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH;

$L^1$ independently represents an ethylene, propylene or butylene group;

n independently represents 0 or an integer or decimal ranging from 1 to 30.

According to the invention, during the polymerization reaction, the monomers can be introduced separately or else in the form of one or more mixtures of these monomers.

Preferably, the monomers are introduced in the form of a mixture.

Preferably according to the invention, the anionic monomer (a) is an anionic monomer comprising a polymerizable vinyl function and at least one carboxylic acid function.

More preferably, it is a monomer chosen from acrylic acid, methacrylic acid, maleic acid, itaconic acid, crotonic acid, an acrylic acid salt, a methacrylic acid salt, a maleic acid salt, an itaconic acid salt, a crotonic acid salt, a cinammic acid salt, and mixtures thereof.

More preferably according to the invention, the anionic monomer (a) is chosen from acrylic acid, methacrylic acid, an acrylic acid salt, a methacrylic acid salt, and mixtures thereof. Even more preferably according to the invention, the anionic monomer (a) is chosen from acrylic acid, methacrylic acid, and mixtures thereof The monomer (a) more particularly preferred is methacrylic acid.

Likewise preferably according to the invention, the anionic monomer (a) is used in an amount of at, least 20 mol %, preferably from 25 to 60 mol %, in particular from 30 to 55 mol %, relative to the total molar amount of monomers.

Preferably according to the invention, the hydrophobic nonionic monomer (b) is a hydrophobic nonionic monomer comprising a polymerizable vinyl function, in particular a monomer which is not an associative monomer.

Advantageously, the hydrophobic nonionic monomer (b) is chosen from acrylic acid esters, methacrylic acid esters, acrylic acid amides, methacrylic acid amides, acrylic acid nitriles and methacrylic acid nitriles, or else from acrylonitrile, styrene, methylstyrene and diisobutylene.

Preferably, the hydrophobic nonionic monomer (b) is chosen from $C_1$-$C_8$-alkyl acrylates, $C_1$-$C_8$-alkyl methacrylates, $C_1$-$C_8$-alkyl maleates, $C_1$-$C_8$-alkyl itaconates, $C_1$-$C_8$-alkyl crotonates, $C_1$-$C_8$-alkyl cinnamates, and mixtures thereof, preferably methyl acrylate, ethyl acrylate, butyl acrylate, 2-ethylhexyl acrylate, methyl methacrylate, ethyl methacrylate, butyl methacrylate, and mixtures thereof. Particularly preferably, the hydrophobic nonionic monomer (b) is chosen from methyl acrylate, ethyl acrylate, butyl acrylate, methyl methacrylate, ethyl methacrylate, and mixtures thereof. The hydrophobic nonionic monomer (b) more particularly preferred is ethyl acrylate.

Likewise preferably according to the invention, the hydrophobic nonionic monomer (b) is used in an amount of from 30 to 80 mol %, preferably from 35 to 75 mol %, more preferentially from 45 to 70 mol %, relative to the total molar amount of monomers.

Particularly preferably, the copolymer (PI) can be produced from anionic monomer (a) chosen from acrylic acid, methacrylic acid and mixtures thereof, preferentially methacrylic acid, and from hydrophobic nonionic monomer (b) chosen from methyl acrylate, ethyl acrylate, butyl acrylate, methyl methacrylate, ethyl methacrylate, and mixtures thereof, preferentially ethyl acrylate.

In addition to the monomers (a) and (b), the production of the copolymer (P1) according to the invention uses at least one monomer of formula (I). This monomer of formula (I) comprises at least two polymerizable ethylenic unsaturations. The monomer of formula (I) is advantageously a cross-linking monomer and more advantageously, a monomer which is not an associative monomer. Particularly essentially, the monomer of formula (I) is a cross-linking monomer of which the two polymerizable ethylenic unsaturations have different properties which confer specific cross-linking properties on the monomer of formula (I).

Preferably, the preparation of the copolymer (P1) according to the invention uses one or two monomers of formula (I), in particular one monomer of formula (I).

For the monomer (c), $L^1$ independently represents an ethylene, propylene or butylene group, namely respectively a CH$_2$—CH$_2$, CH(CH$_3$)—CH$_2$ and CH(CH$_2$CH$_3$)—CH$_2$ group.

Preferably according to the invention, the monomer (c) is a compound of formula (I) wherein n represents an integer or decimal ranging from 1 to 18, from 1 to 15, or from 2 to 16 or else from 2 to 12.

Particularly preferably according to the invention, the monomer (c) is a compound (c1) of formula (I) wherein $R^1$ represents H, $R^2$ represents —C(H)=CH$_2$, $L^1$ represents CH$_2$—CH$_2$ and n represents 10 (CAS number 99742-80-0). Likewise particularly preferably according to the invention, the monomer (c) is a compound (c2) of formula (I) wherein $R^1$ represents H, $R^2$ represents —C(CH$_3$)=CH$_2$, $L^1$ represents CH$_2$—CH$_2$ and n represents 3.5 (CAS number 121826-50-4).

Likewise particularly preferably according to the invention, the monomer (c) is a compound (c3) of formula (I) wherein $R^1$ represents H, $L^1$ represents CH$_2$—CH$_2$, $R^2$ represents —C(CH$_3$)=CH$_2$ and n represents 10 (CAS number 121826-50-4). These compounds of formula (I) are known as such and can be produced according to the methods described in the prior art or according to methods which can be adapted from the methods described in the prior art.

Likewise preferably according to the invention, the monomer (c) is used in an amount of less than 5 mol %, preferably from 0.01 to 5 mol % and more preferentially from 0.02 to 4 mol %, or from 0.02 to 2 mol % or else from 0.04 to 0.5 mol % or from 0.04 to 0.25 mol % of momomer (c) relative to the total molar amount of monomers.

The monomer (c) is generally known as such or else it can be produced using the preparation methods described in patent application US 2006-0052564.

According to the invention, the copolymer (P1) is produced by a polymerization reaction comprising the use of monomers (a) and (b) and of monomer (c) of formula (I). The copolymer (P1) can therefore be produced from solely these monomers (a), (b) and (c) of formula (I).

The copolymer (P1) can also be produced from these three types of monomers combined with other monomers. Thus, in addition to the monomers (a) and (b) and the monomer (c) of formula (I), the polymerization reaction for producing the copolymer (P1) can use one or more other monomers.

Advantageously, the copolymer (P1) can be produced by a polymerization reaction also using at least one nonionic monomer (d), different than the monomer (b), comprising a polymerizable vinyl function and a hydrocarbon-based chain comprising at least 10 carbon atoms. According to the invention, the nonionic monomer (d) is preferably chosen from:

a monomer (d1) comprising a polymerizable vinyl function and a $C_{12}$-$C_{36}$ hydrocarbon-based chain;

a monomer (d2) comprising a polymerizable vinyl function, a $C_{12}$-$C_{36}$ hydrocarbon-based chain and from 1 to 150, preferably from 15 to 50 and more preferentially from 20 to 30, alkyleneoxy groups.

For the nonionic monomer (d2), the preferred oxyalkylene groups are ethoxy (OE), propoxy (PO) and butoxy (BO) groups, in particular the ethoxy (OE) group. A preferred nonionic monomer (d2) is a compound of formula (II):

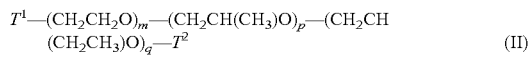

wherein:
$T^1$ independently represents a polymerizable vinyl function,
$T^2$ independently represents:
- a hydrocarbon-based chain comprising at least 10 carbon atoms, preferably a $C_{12}$-$C_{36}$ hydrocarbon-based chain; or
- a hydrocarbon-based chain comprising at least 10 carbon atoms, preferably a $C_{12}$-$C_{36}$ hydrocarbon-based chain, and at least one heteroatom chosen from O, S, N and P; or
- m, p and q, which may be identical or different, independently represent an integer or decimal ranging from 0 to 150, the sum of m, p and q being non-zero.

Preferably, $T^1$ represents a, polymerizable vinyl function chosen from a vinyl group, a methylvinyl group, an acrylate group, a methacrylate group, an allyl group and a methallyl group.

As particular compound (d2), mention may be made of the compound (d2-1) of formula (II) wherein $T^1$ represents a —OC(O)C(CH$_3$)=CH$_2$ group, $T^2$ represents a branched hydrocarbon-based chain comprising 16 carbon atoms (2-hexyldecanyl), m represents 25 and p and q represent 0.

Likewise advantageously, the polymerization reaction can use from 0.01 to 10 mol % of monomer (d), relative to the total molar amount of monomers. Preferably, the polymerization reaction can use from 0.02 to 5 mol % or from 0.02 to 2 mol % of monomer (d), relative to the total molar amount of monomers.

Advantageously, the copolymer (P1) can be produced by a polymerization reaction also using at least one ionic or nonionic monomer (e), different than the monomer (b).

Preferably, according to the invention, the ionic or nonionic monomer (e) is chosen from:
- 2-acrylamido-2-methylpropane sulfonic acid or a salt thereof;
- telomers, preferably dimers, trimers or tetramers, which are unsaturated, of acrylic acid;
- the monomers of formula (III):

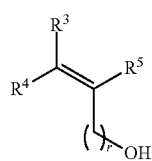

wherein:
$R^3$, $R^4$ and $R^5$, which may be identical or different, independently represent H or CH$_3$;
r independently represents 1, 2 or 3;
the monomers of formula (IV):

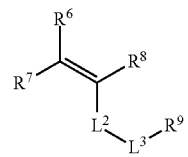

wherein:
$R^6$, $R^7$ and $R^8$, which may be identical or different, independently represent H or CH$_3$;
$R^9$ represents H or CH$_3$;
$L^2$ independently represents a direct bond or a group chosen from O, C(=O)CH$_2$CH$_2$ and CH$_2$;
$L^3$ independently represents a direct bond or from 1 to 150, preferably from 15 to 50 and more preferentially from 25 to 30 alkyleneoxy groups.

For the ionic or nonionic monomer (e), the preferred oxyalkylene groups are ethoxy (OE), propoxy (PO) and butoxy (BO) groups, in particular the ethoxy (OE) group.

According to the invention, an ethoxy (OE) group is a —CH$_2$—CH$_2$—O residue, a propoxy (PO) group is an ethoxy group substituted, with a methyl radical on one of the carbon atoms as a replacement for a hydrogen atom, and a butoxy (BO) group is an ethoxy group substituted with an ethyl radical on one of the carbon atoms as a replacement for a hydrogen atom.

According to the invention, among the preferred monomers (e) of formula (IV), the following are known:
- HEMA or hydroxyethyl methacrylate, which is a compound of formula (IV) wherein $R^6$, $R^7$ and $R^9$ represent H, $R^8$ represents CH$_3$, $L^2$ represents. C(O)O and $L^3$ represents an ethyleneoxy group; and
- HPMA or hydroxypropyl methacrylate, which is a compound of formula (IV) wherein $R^6$, $R^7$ and $R^9$ represent H, $R^8$ represents CH$_3$, $L^2$ represents C(O)O and $L^3$ represents a propyleneoxy group;
- HPA or hydroxypropyl acrylate, which is a compound of formula (IV) wherein $R^6$, $R^7$, $R^8$ and $R^9$ represent H, $L^2$ represents C(O)O and $L^3$ represents a propyleneoxy group.

Likewise advantageously, the polymerization reaction can use from 0.01 to 25 mol % of monomer (e), relative to the total molar amount of monomers. Preferably, the polymerization reaction can use from 0.02 to 15 mol % or from 0.02 to 10 mol % of monomer (e), relative to the total molar amount of monomers.

Advantageously, the copolymer (P1) can be produced by a polymerization reaction also using at least one other monomer (f). The monomer (f) is advantageously a hydrophilic, hydrophobic or amphiphilic cross-linking monomer and it is generally a compound comprising several ethylenic unsaturations. It is distinct from the monomer of formula (I) according to the invention. The monomer (f) can be a compound chosen from:
a compound of formula or formula (VI)

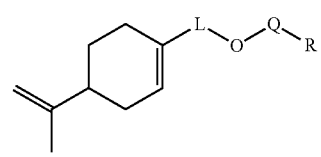

wherein:

L represents $CH_2$, monoalkoxylated CH, or polyalkoxylated $CH_2$;

Q represents a direct or C(O) bond;

R represents $-C(H)=CH_2$, $-C(CH_3)=CH_2$, $-C(H)=C(H)C(O)OH$, $-C(H)=C(H)CH_3$, $-C(=CH_2)CH_2C(O)OH$, $-CH_2C(=CH_2)C(O)OH$, $Q^3OQ^4OC(O)C(CH_3)=CH_2$ or $Q^3OQ^4OC(O)C(H)=CH_2$;

$Q^3$ represents a divalent residue of an asymmetric diisocyanate compound, preferably chosen from tolyl. 1,3-diisocyanate (TDI) and isophorone diisocyanate (IPDI);

$Q^4$ represents $CH_2$, $CH_2-CH_2$, monoalkoxylated $CH_2$, monoalkoxylated $CH_2-CH_2$, polyalkoxylated $CH_2$ or polyalkoxylated $CH_2-CH_2$;

a compound of formula (VI-A)

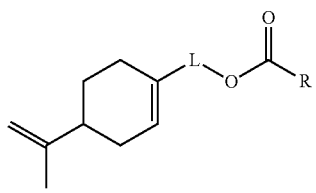

(VI-A)

wherein:

L represents $CH_2$, monoalkoxylated $CH_2$ or polyalkoxylated $CH_2$;

R represents $-C(H)=CH_2$, $-C(CH_3)=CH_2$, $-C(H)=C(H)C(O)OH$, $-C(H)=C(H)CH_3$, $-C(=CH_2)CH_2C(O)OH$, $-CH_2C(=CH_2)C(O)OH$, $Q^3OQ^4OC(O)C(CH_3)=CH_2$ or $Q^3OQ^4OC(O)C(H)=CH_2$;

$Q^3$ represents a divalent residue of an asymmetric diisocyanate compound, preferably chosen from tolyl 1,3-diisocyanate (TDI) and isophorone diisocyanate (IPDI);

$Q^4$ represents $CH_2$, $CH_2-CH_2$, monoalkoxylated $CH_2$, monoalkoxylated $CH_2-CH_2$, polyalkoxylated $CH_2$ or polyalkoxylated $CH_2-CH_2$;

a compound of formula (VI-B):

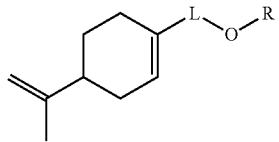

(VI-B)

wherein:

L represents $CH_2$, monoalkoxylated $CH_2$ or polyalkoxylated $CH_2$;

R represents $-C(H)=CH_2$, $-C(CH_3)=CH_2$, $-C(H)=C(H)C(O)OH$, $-C(H)=C(H)CH_3$, $-C(=CH_2)CH_2C(O)OH$, $-CH_2C(=CH_2)C(O)OH$, $Q^3OQ^4OC(O)C(CH_3)=CH_2$ or $Q^3OQ^4OC(O)C(H)=CH_2$;

$Q^3$ represents a divalent residue of an asymmetric diisocyanate compound, preferably chosen from tolyl 1,3-diisocyanate (TDI) and isophorone diisocyanate. (IPDI);

$Q^4$ represents $CH_2$, $CH_2-CH_2$, monoalkoxylated $CH_2$, monoalkoxylated $CH_2-CH_2$; polyalkoxylated $CH_2$ or polyalkoxylated $CH_2-CH_2$.

The monomer (f) can also be chosen from di(meth)acrylates such as polyalkylene glycol di(meth)acrylate, in particular polypropylene glycol di(meth)acrylate, ethylene glycol di(meth)acrylate, polyethylene glycol di(meth)acrylate, triethylene glycol di(meth)acrylate, 1,3-butylene glycol di(meth)acrylate, 1,6-butylene glycol, di(meth)acrylate, 1,6-hexanediol di(meth)acrylate, neopentyl glycol di(meth)acrylate or 1,9-nonanediol di(meth)acrylate, but also 2,2'-bis(4-(acryloxypropyloxy)-phenyl)propane, 2,2'-bis(4-(acryloxydiethoxy)-phenyl)propane and zinc acrylate; tri(meth)acrylate compounds, such as trimethylolpropane tri(meth)acrylate and ethoxylated trimethylolpropane tri(meth)acrylate, trimethylolethane tri(meth)acrylate, pentaerythritol tri(meth)acrylate and tetramethylolmethane tri(meth)acrylate; tetra(meth)acrylate compounds, such as ditrimethylolpropane tetra(meth)acrylate, tetramethylolmethane tetra(meth)acrylate and pentaerythritol tetra(meth)acrylate; hexa(meth)acrylate compounds, such as dipentaerythritol hexa(meth)acrylate; penta(meth)acrylate compounds, such as dipentaerythritol penta(meth)acrylate; allyl compounds; such as allyl (meth)acrylate, diallyl phthalate, diallyl itaconate, diallyl fumarate, diallyl maleate; polyallyl ethers of sucrose having from 2 to 8 groups per molecule, pentaerythritol polyallyl ethers, such as pentaerythritol diallyl ether, pentaerythritol triallyl ether and pentaerythritol tetraallyl ether; trimethylolpropane polyallyl ethers, such as trimethylolpropane diallyl ether and trimethylolpropane triallyl ether. Other polyunsaturated compounds include divinyl glycol, divinylbenzene, divinylcyclohexyl and methylenebisacrylamide.

The monomer (f) can also be produced by a reaction for esterification of a polyol with an unsaturated anhydride such as acrylic anhydride, methacrylic anhydride, maleic anhydride or itaconic anhydride. In order to obtain the monomer (f), use may also be made of compounds chosen from polyhaloalkanols such as 1,3-dichloroisopropanol and 1,3-dibromoisopropanol; haloepoxyalkanes such as epichlorohydrin, epibromohydrin, 2-methyl epichlorohydrin and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ether, bisphenol A-epichlorohydrin epoxy resin, and mixtures thereof.

The monomer (f) can also be chosen from trifunctional cross-linking agents. It may in particular be trimethylolpropane tri(meth)acrylate (TMPTA) or ethoxylated trimethylolpropane tri(meth)acrylate (such as, for example, TMPTA 3OE).

The monomer (f) may also be chosen from trimethylolpropane tri(meth)acrylate, ethoxylated trimethylolpropane tri(meth)acrylate, ethylene glycol di(meth)acrylate, methylenebisacrylamide, diallyl phthalate, diallyl maleate, and mixtures thereof.

The monomer (f) may also be a mixture of two distinct monomers, for example EGDCPEA (ethylene glycol dicyclopentenyl ether acrylate) and TMPTA or else EGDCPEA and TMPTA 3OE.

According to the invention, the monomer (f) is preferably chosen from a compound of formula (V), trimethylolpropane trimethacrylate, trimethylolpropane triacrylate, ethoxylated trimethylolpropane trimethacrylate, ethoxylated trimethylolpropane triacrylate, ethylene glycol dimethacrylate, ethylene glycol diacrylate, methylenebisacrylamide, diallyl phthalate, diallyl maleate, and mixtures thereof.

Likewise advantageously, the polymerization reaction can use less than 5 mol %, preferably from 0.01 to 4 mol %, in particular from 0.02 to 4 mol % or from 0.02 to 2 mol %, in particular from 0.04 to 1 mol % of monomer (f), relative to the total molar amount of monomers.

Likewise advantageously, the copolymer (P1) can be produced by a polymerization reaction also using at least one monomer (g). The monomer (g) is advantageously a hydrophilic, hydrophobic or amphiphilic cross-linking monomer and it is, generally a compound comprising several ethylenic unsaturations. It is distinct from the monomer of formula (I) according to the invention. The monomer (g) can be a compound of formula (VI):

a compound of formula of formula (VI):

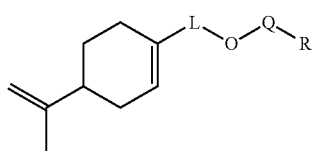
(VI)

wherein:
L represents $CH_2$, monoalkoxylated $CH_2$ or polyalkoxylated $CH_2$;
Q represents a direct or C(O) bond;
R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=CH2)C(O)OH, $Q^3OQ^4OC(O)C(CH_3)$=$CH_2$ or $Q^3OQ^4OC(O)C(H)$=$CH_2$;
$Q^3$ represents a divalent residue of an asymmetric diisocyanate compound, preferably chosen from tolyl 1,3-diisocyanate (TDI) and isophorone diisocyanate (IPDI);
$Q^4$ represents $CH_2$, $CH_2$—$CH_2$, naonoalkoxylated $CH_2$, monoalkoxylated $CH_2$—$CH_2$, polyalkoxylated $CH_2$ or polyalkoxylated $CH_2$—$CH_2$;

a compound of formula (VI-A):

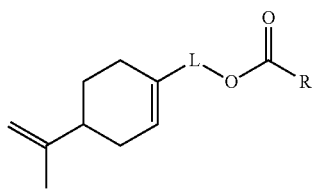
(VI-A)

wherein:
L represents $CH_2$, monoalkoxylated $CH_2$ or polyalkoxylated $CH_2$;
R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —CH2C(=$CH_2$)C(O)OH, $Q^3OQ^4OC(O)C(CH_3)$=$CH_2$ or $Q^3OQ^4OC(O)C(H)$=$CH_2$;
$Q^3$ represents a divalent residue of an asymmetric diisocyanate compound, preferably chosen from tolyl 1,3-diisocyanate (TDI) and isophorone diisocyanate (IPDI);
$Q^4$ represents $CH_2$, CH2—$CH_2$, monoalkoxylated $CH_2$, monoalkoxylated $CH_2$—$CH_2$, polyalkoxylated $CH_2$ or polyalkoxylated $CH_2$—$CH_2$; polyalkoxylated $CH_2$ or polyalkoxylated $CH_2$—$CH_2$;
a compound of formula (VI-B):

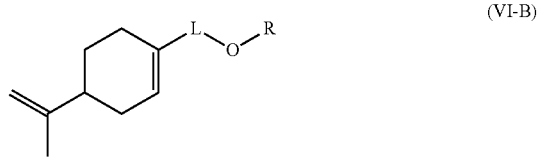
(VI-B)

wherein:
L represents $CH_2$, monoalkoxylated $CH_2$ or polyalkoxylated $CH_2$;
R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH, $Q^3OQ^4OC(O)C(CH_3)$=$CH_2$ or $Q^3OQ^4OC(O)C(H)$=$CH_2$;
$Q^3$ represents a divalent residue of an asymmetric diisocyanate compound, preferably chosen from tolyl 1,3-diisocyanate (TDI) and isophorone diisocyanate (IPDI);
$Q^4$ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$.

These compounds of formula (VI), (VI-A) or (VI-B) can be produced according to a process comprising the reaction according to Scheme 1 during which the temperature is generally between 50° C. and 250° C. and which can use a radical-inhibiting agent Scheme 1

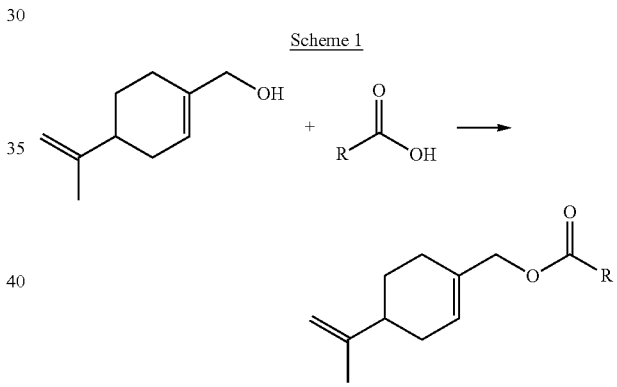

Likewise advantageously, the polymerization reaction can use less than 5 mol %, preferably from 0.01 to 4 mol %, in particular from 0.02 to 2 mol %, in particular from 0.04 to 1 mol % of monomer (g), relative to the total molar amount of monomers.

In addition to the various monomers, the production of the copolymer (P1) also uses at least one chain-transfer agent, preferably chosen from mercaptan compounds, in particular mercaptan compounds comprising at least four carbon atoms, such as butylmercaptan, n-octylmercaptan, n-dodecylmercaptan, or tert-dodecylmercaptan.

The copolymer (P1) produced according to the invention is therefore obtained by a polymerization reaction. This reaction can be a radical polymerization reaction, for example an emulsion, dispersion or solution polymerization reaction. The polymerization can be carried out in a solvent, in the presence of at least one initiator compound. As examples of initiator compounds, persulfate salts, in particular ammonium persulfate, are known.

Preferably, the reaction is a radical emulsion polymerization reaction. The radical-emulsion polymerization can be carried out in the presence of .at least one surfactant compound and optionally of at least one chain-transfer agent, for generally regulating the molecular mass of the chains produced during the polymerization. As surfactant compounds which can be used, the following are known:

anionic surfactants, for example a fatty acid salt, an alkyl sulfate salt such as sodium lauryl sulfate, an alkyl ether sulfate salt such as sodium lauryl ether sulfate, an alkylbenzenesulfonate salt such as sodium dodecylbenzenesulfonate, an alkyl phosphate salt or a sulfosuccinate diester salt, a cocoamphoacetate salt such as sodium cocoamphoacetate, a cocoamphodiacetate salt such as sodium cocoamphodiacetate, a lauroyl glutamate salt such as sodium lauroyl glutamate, a cocoyl isethionate salt such as sodium cocoyl isethionate; a lauroyl methyl isethionate salt such as sodium lauroyl methyl isethionate, a methyl cocoyl taurate salt such as sodium methyl cocoyl taurate, a methyl oleyl taurate salt such as sodium methyl oleyl taurate, a lauroyl sarcosinate salt such as sodium lauroyl sarcosinate, a laureth 3 sulfosuccinate salt such as sodium laureth 3 sulfosuccinate, a cocoyl apple amino acid salt such as sodium cocoyl apple aminate, a cocoyl oat amino acid salt such as sodium cocoyl oat aminate;

nonionic surfactants, for example a polyoxyethylene alkyl ether or a polyoxyethylene fatty acid ester;

cationic surfactants, for example quaternary alkyl ammonium halides and quaternary aryl ammonium halides;

zwitterionic or amphoteric surfactants, for example surfactants comprising a betaine group; and mixtures thereof.

The invention also relates to the use, for the production of a copolymer, of less than 5 mol %, relative to the total molar amount of monomers used, of at least one monomer of formula (I):

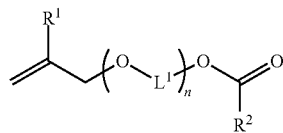

(I)

wherein:
$R^1$ independently represents H or $CH_3$;
$R^2$ independently represents
—C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH;
$L^1$ independently represents an ethylene, propylene or butylene group;
n independently represents 0 or an integer or decimal ranging from 1 to 30.

Likewise, the invention relates to the use, for the cross-linking of a polymer or of a mixture of monomers, of less than 5 mol %, relative to the total molar amount of monomers used, of at least one monomer of formula (I):

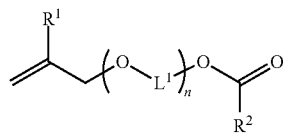

(I)

wherein:
$R^1$ independently represents H or $CH_3$;
$R^2$ independently represents
—C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH;
$L^1$ independently represents an ethylene, propylene or butylene group;
n independently represents 0 or an integer or decimal ranging from 1 to 30.

These uses according to the invention can likewise be defined according to the features of production of the copolymer (P1) according to the invention.

In addition to this copolymer (P1) and the use thereof, the invention also relates to a process for producing this copolymer according to the invention. Thus, the invention provides a process (1) for producing a copolymer (P1) by a reaction for polymerization:

(a) of at least one anionic monomer comprising at least one polymerizable ethylenic unsaturation, preferably an anionic monomer comprising a polymerizable vinyl function and at least one carboxylic acid function; and (b) of at least one hydrophobic nonionic monomer comprising at least one polymerizable ethylenic unsaturation, preferably a hydrophobic nonionic monomer comprising a polymerizable vinyl function; and (c) of at least one monomer of formula (I):

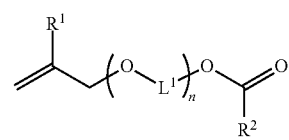

(I)

wherein:
$R^1$ independently represents H or $CH_3$;
$R^2$ independently represents
—C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH;
$L^1$ independently represents an ethylene, propylene or butylene, group;
n independently represents 0 or an integer or decimal ranging from 1 to 30.

The process (1) according to the invention is also defined by the monomers and by the conditions used for the production of the copolymer (P1) according to the invention.

The invention also relates to a process (2) for producing a copolymer (P2) obtained by a polymerization reaction also comprising the use, during the polymerization reaction, of a copolymer (P1), obtained beforehand during the polymerization reaction of the process (1) according to the invention.

Thus, the process (2) according to the invention comprises the reaction for polymerization of a copolymer (p1) produced beforehand according to the invention with:

(a) at least one anionic monomer comprising at least one polymerizable ethylenic unsaturation, preferably an anionic monomer comprising a polymerizable vinyl function and at least one carboxylic acid function; and (b) at least one hydrophobic nonionic monomer comprising at least one polymerizable ethylenic unsaturation, preferably a hydrophobic nonionic monomer comprising a polymerizable vinyl function; and (c) at least one monomer of formula (I):

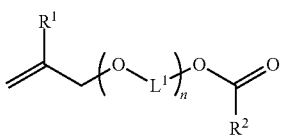

(I)

wherein:
$R^1$ independently represents H or $CH_3$;
$R^2$ independently represents $-C(H)=CH_2$, $-C(CH_3)=CH_2$, $-C(H)=C(H)C(O)OH$, $-C(H)=C(H)CH_3$, $-C(=CH_2)CH_2C(O)OH$, $-CH_2C(=CH_2)C(O)OH$;
$L^1$ independently represents an ethylene, propylene or butylene group;
n independently represents 0 or an integer or decimal ranging from 1 to 30.

The process (2) according to the invention is also defined by the monomers and by the conditions used for the production of the copolymer (P1) according to the invention.

Advantageously, the multiphase copolymer (P2) according to the invention can be produced sequentially, by emulsion, dispersion or solution radical polymerization.

Preferably, at least two consecutive steps are carried out, a first step which makes it possible to obtain a first copolymer (P1), and then a second polymerization step uses a copolymer (P1).

In practice, the first step consists in bringing the monomers for producing the copolymer (P1) into contact with a polymerization initiator compound. This contacting can be carried out in discontinuous mode, in batch mode, or else in semi-batch mode or in semi-continuous mode. This contacting can be carried out over a period of time which can range from several minutes to several hours.

The second step of producing the copolymer (P2) can comprise:
the addition of the monomers for producing the copolymer (P2) to a dispersion medium comprising the copolymer (P1) already formed, for example according to a discontinuous mode, a batch mode, a semi-batch mode or, a semi-continuous mode, and according to a period of time which can range from several minutes to several hours, and
simultaneously for the semi-continuous mode or subsequently for the discontinuous mode, the introduction of a polymerization initiator compound.

This step then allows the formation of a copolymer (P2) according to the invention.

The invention therefore also relates to the copolymer (P2) which can be obtained according to the process (2) according to the invention.

Advantageously, the copolymer (P2) according to the invention is multiphase. Likewise advantageously, the copolymer (P2) according to the invention comprises a core comprising a first copolymer (P1), totally or partially covered with a second copolymer (P1), which may be identical to or different than the first copolymer (P1).

Preferably, the copolymer (P2) according to the invention comprises a core comprising, a first copolymer (P1), totally or partially covered with a second copolymer (P1) for which the 1° copolymer (P1)/2° copolymer (P1) weight ratio is between 45/55 and 95/5, in particular between 60/40 and 90/10.

The copolymers according to the invention proved to be particularly efficient as rheology-modifying agents in a broad range of aqueous compositions or else as thickening and suspending agent. Mention may be made of the aqueous compositions in many industrial fields and in particular fracking fluids in drilling, formulations for ceramics, paper coating colours. Mention is in particular made of washing compositions containing surfactants, such as personal care compositions or homecare compositions comprising for example cosmetic compositions, personal hygiene compositions, toiletry products and cleaning compositions for application to the body (including the skin, the hair, the nails) of human beings or of animals, for example shampoo compositions, or else compositions used for cleaning or maintaining sanitary conditions, for example in the kitchen, the bathroom, detergent products, laundry products, etc.

The copolymers (P1) and (P2) according to the invention have advantageous properties. They can therefore be integrated into aqueous compositions. Thus, the invention also provides an aqueous composition comprising at least one copolymer (P1) according to the invention. The invention also provides an aqueous composition comprising at least one copolymer (P2) according to the invention. The invention also provides an aqueous composition comprising at least one copolymer (P1) according to the invention and at least one copolymer (P2) according to the invention.

Preferably, the aqueous composition according to the invention is a cosmetic composition and can comprise:
at least one copolymer (P1) according to the invention; or
at least one copolymer (P2) according to the invention; or
at least one copolymer (P1) according to the invention and at least one copolymer (P2) according to the invention.

Within the composition according to the invention, the copolymers (P1) and (P2) according to the invention may be present in amounts ranging from 0.1% to 20% by weight, in particular from 0.5% to 1.2% by weight, relative to the total weight, of the composition.

In addition to a copolymer according to the invention, the composition according to the invention can comprise a limpid continuous phase and suspended particles distributed in the continuous phase. The copolymer according to the invention can then confer clarity on the composition and can maintain in suspension particles that are present.

When it is used, such a composition according to the invention generally requires no mixing step, even if the composition has been stored for several weeks, or even several. months.

The composition according to the invention can also comprise one or more surfactant compounds, in particular chosen from anionic, zwitterionic or amphoteric, cationic or nonionic surfactants and mixtures thereof It can also comprise one or more active ingredients.

More preferably, the cosmetic composition according to the invention has a pH ranging from 3 to 9. Even more preferably, its pH ranges from 3 to 7. Even more preferentially, its pH ranges from 4 to 7.

The invention thus' relates to the use, for producing an aqueous composition according to the invention or for producing a cosmetic composition according to the invention:
of at least one copolymer (P1) according to the invention; or
of at least one copolymer (P2) according to the invention; or
of at least one copolymer (P1) according to the invention and of at least one copolymer (P2) according to the invention.

EXAMPLES

The examples which follow make it possible to illustrate the various aspects of the invention.

The following abbreviations are used:
MAA: methacrylic acid,
EA: ethyl acrylate,
SR 351 from Sartomer: trimethylolpropane triacrylate (TMPTA),
Sipomer HPM100 from Solvay-Rhodia: nopol methacrylate 10 OE,
Polyglykol B11/50 from Clariant: ethylene oxide-propylene oxide-monobutyl ether,
Empicol LXVN from Huntsmann: sodium lauryl sulfate (SDS),
Texapon NS0 from BASF: ammonium laureth sulfate at 28% in solution or ammonium lauryl ether sulfate at 28% in solution (SLES),
sodium persulfate $(NH_4)S_2O_8$,
compound (d): solution comprising 45% by weight of methacrylic acid, 5% by weight of water and 50% by weight of compound (d2-1) of formula (II) wherein. $T^1$ represents a —OC(O)C(CH$_3$)=CH$_2$ group, $T^2$ represents a branched hydrocarbon-based chain comprising 16 carbon atoms (2-hexyldecanyl), m represents 25 and p and q represent 0.

Production of the Polymers According to a Semi-Batch Process

The reagents and amounts used are presented in table 1.
In a stirred 1 l reactor heated using an oil bath, the mixture 1 is prepared by introducing deionized water and a solution containing 28% by mass of sodium lauryl ether sulfate (SLES) or sodium lauryl sulfate (SDS), and optionally ethylene oxide-propylene oxide-monobutyl ether.
A mixture 2, referred to as premix, comprising the following, is prepared in a beaker:

methacrylic acid,
ethyl acrylate,
compound (c), or Sipomer HPM100 TMPTA,
optionally, compound (d),
optionally, deionized water,
optionally, solution at 28% of sodium lauryl ether sulfate (SLES) or of sodium, lauryl sulfate (SDS),
optionally, ethylene oxide-propylene oxide-monobutyl ether.

This premix is stirred in order to form a monomeric mixture.

Similarly, a comparative premix not comprising compound (c) is prepared.

A solution of initiator 1 comprising ammonium persulfate and deionized water is prepared. A solution of initiator 2 also comprising ammonium persulfate and deionized water is prepared.

The solution of initiator 1 and also the monomer premix is injected, in parallel, over the course of 2 hours, into the reactor heated to the temperature of 85° C.±1° C. Next, over the course of 1 hour, the solution of initiator 2 is injected into the reactor heated to 85° C.±1° C.

Water is optionally added and the mixture is cured for 30 min at the temperature of 85° C.±1° C. The whole mixture is then cooled to ambient temperature.

The polymers according to the invention and the comparative polymers were produced under these conditions by varying the monomer compositions of the monomer premixes. The compositions of the copolymers obtained are given in the table 1.

TABLE 1

| | | 1 | 2 | 3 | 4 | 5 | 6 | 7 | 8 | 9 | 10 | 11 | 12 |
|---|---|---|---|---|---|---|---|---|---|---|---|---|---|
| | | \multicolumn{12}{c}{Example} | | | | | | | | | | | | |
| | | According to the invention | | | | | | | | | Comparative | | |
| Component (c) | | (c1) | (c1) | (c1) | (c1) | (c2) | (c2) | (c1) | (c1) | (c1) | 0 | TMPTA | Sipomer HPM100 |
| Mixture 1 | Water | 400 | 400 | 400 | 400 | 400 | 400 | 400 | 400 | 432 | 432 | 432 | 400 |
| | SDS | 2.6 | 2.6 | 2.6 | 2.6 | 2.6 | 2.6 | 2.6 | 2.6 | 0 | 0 | 0 | 2.6 |
| | SLES | 0 | 0 | 0 | 0 | 0 | 0 | 0 | 0 | 9.29 | 9.29 | 9.29 | 0 |
| | B11/50 | 1.1 | 1.1 | 1.1 | 1.1 | 1.1 | 1.1 | 1.1 | 1.1 | 0 | 0 | 0 | 1.1 |
| Mixture 2 | Water | 173.7 | 173.7 | 173.7 | 173.7 | 173.7 | 173.7 | 173.7 | 173.7 | 26.00 | 26.06 | 172.50 | 173.7 |
| | SDS | 1.81 | 1.81 | 1.81 | 1.81 | 1.81 | 1.81 | 1.81 | 1.81 | 0 | 0 | 0 | 1.81 |
| | SLES | 0 | 0 | 0 | 0 | 0 | 0 | 0 | 0 | 0 | 0 | 6.47 | 0 |
| | B11/50 | 1.04 | 1.04 | 1.04 | 1.04 | 1.04 | 1.04 | 1.04 | 1.04 | 0 | 0 | 0 | 1.04 |
| | Compound (a) MAA | 105.69 | 105.69 | 105.69 | 105.69 | 105.69 | 105.69 | 105.69 | 99.74 | 76.31 | 76.31 | 76.66 | 99.74 |
| | Compound (b) EA | 191.28 | 191.28 | 191.28 | 191.28 | 191.28 | 191.28 | 191.28 | 191.28 | 196.10 | 196.10 | 196.82 | 191.28 |
| | Compound (c) | 2.75 | 0.83 | 1.925 | 2.33 | 1.925 | 1.1 | 3.44 | 2.75 | 1.10 | 0.00 | 1.00 | 2.75 |
| | Compound (d2-1) | 0 | 0 | 0 | 0 | 0 | 0 | 0 | 12.8 | 51.91 | 51.91 | 51.91 | 12.8 |
| Initiator 1 | $(NH_4)_2S_2O_8$ | 0.587 | 0.587 | 0.587 | 0.587 | 0.587 | 0.587 | 0.587 | 0.587 | 0.467 | 0.467 | 0.467 | 0.587 |
| | Water | 58 | 59 | 60 | 61 | 65 | 67 | 62 | 57 | 55 | 55 | 55 | 55 |
| Initiator 2 | $(NH_4)_2S_2O_8$ | 0.123 | 0.123 | 0.123 | *0.123 | 0.123 | 0.123 | 0.123 | 0.123 | 0.123 | 0.123 | 0.123 | 0.123 |
| | Water | 40 | 40 | 40 | 40 | 40 | 40 | 40 | 40 | 20 | 20 | 20 | 40 |
| Rinsing or adjustment | Water | 20 | 20 | 20 | 20 | 20 | 20 | 20 | 20 | 11.25 | 15 | 15 | 20 |
| Composition by mass of the polymer % | Residue compound (a) MAA | 35.26 | 35.49 | 35.36 | 35.31 | 35.36 | 35.46 | 35.18 | 34.55 | 31.11 | 31.21 | 31.12 | 34.55 |
| | Residue compound (b) EA | 63.82 | 64.23 | 64.00 | 63.91 | 64.00 | 64.17 | 63.67 | 62.52 | 60.73 | 60.94 | 60.77 | 62.52 |
| | Residue compound (c) | 0.92 | 0.28 | 0.64 | 0.78 | 0.64 | 0.37 | 1.15 | 0.90 | 0.34 | 0.00 | 0.31 | 0.90 |
| | Residue compound (d2-1) | 0.00 | 0.00 | 0.00 | 0.00 | 0.00 | 0.00 | 0.00 | 2.04 | 7.82 | 7.85 | 7.80 | 2.04 |
| Molar | Residue | 39.05 | 39.10 | 39.07 | 39.06 | 39.03 | 39.07 | 39.04 | 39.00 | 37.09 | 37.12 | 37.07 | 39.01 |

TABLE 1-continued

| | | 1 | 2 | 3 | 4 | 5 | 6 | 7 | 8 | 9 | 10 | 11 | 12 |
|---|---|---|---|---|---|---|---|---|---|---|---|---|---|
| | | | | | | | Example | | | | | | |
| | | According to the invention | | | | | | | | Comparative | | | |
| composition of the polymer % | compound (a) MAA Residue | 60.79 | 60.85 | 60.82 | 60.80 | 60.75 | 60.81 | 60.76 | 60.70 | 62.27 | 62.31 | 62.25 | 60.72 |
| | compound (b) EA Residue | 0.16 | 0.05 | 0.11 | 0.13 | 0.22 | 0.12 | 0.20 | 0.16 | 0.06 | 0.00 | 0.11 | 0.13 |
| | compound (c) Residue | 0.00 | 0.00 | 0.00 | 0.00 | 0.00 | 0.00 | 0.00 | 0.14 | 0.57 | 0.57 | 0.57 | 0.14 |
| | compound (d2-1) Residue | | | | | | | | | | | | |

Evaluation of the Properties of the Polymers in an Aqueous Formulation

The aqueous formulation used comprises 2.4% or 3% by weight of polymer (see table 1), 9% by weight of a first surfactant compound (SLES or sodium lauryl ether sulfate), 3% by weight of a second surfactant compound (CAPS or cocamidopropyl betaine) and water (qsf 100% by weight). The pH of the formulation is adjusted to a value of 5, 6 or 7 by adding lactic acid or sodium hydroxide.

The formulations are evaluated for their viscosity, clarity and suspending performance properties.

Viscosity

The viscosity of the formulations is measured using a Brookfield viscometer, model LVT. Before measuring the viscosity, each of the formulations is left to stand for 24 hours at 25° C. The spindle of the viscometer must be centered relative to the opening of the formulation flask. The viscosity is measured at 6 revolutions per minute using the appropriate module. The viscometer is allowed to, revolve until the viscosity value is stabilized.

The copolymer which is a rheology-modifying agent must give the formulation in which it is used a sufficient viscosity. In general, the viscosity desired for thickened formulations should be greater than 4,000 mPa·s, in particular greater than 6,000 mPa·s and more particularly greater than 8,000 mPa·s.

Clarity

The clarity of each formulation is evaluated by measuring the transmittance by means of a UV Genesys 10 UV spectrometer (Cole Parmer), equipped with Rotilabo-Einmal Kuvetten PS cuvettes of 4.5 ml. The apparatus is preheated for 10 minutes before use, then a first measurement is carried out by means of a cuvette filled with 3.8 ml of bi-permutated water.

A measurement is then carried out with a cuvette filled with 3.8 ml of cosmetic formulation to be tested. The transmittance is measured at the wavelength of 500 nm. The higher the transmittance value, expressed as a percentage, the more limpid the cosmetic composition. For a transmittance value at 500 nm of at least 60%, the formulation is limpid.

Suspending Performance Levels

Viscoelasticity measurements are carried out on the formulations using a Haake-Mars III rheometer. The variations in Tan($\delta$) and in G' as a function of the strain $\tau$ (scanning of 0 dyn/cm$^2$ to 1000 dyn/cm$^2$) are measured at 25° C. using a 1° Cone/Plan geometry. The values of Tan($\delta$) and of G' at 10 dyn/cm$^2$ and the value of elastic strength are deduced from this measurement.

As a general rule, the formulations have good suspending properties for combined values of G'>50 Pa, of Tan($\delta$) <0.55 and of elastic strength >70 dyn/cm$^2$.

The results obtained are shown in table 2.

It is noted that the copolymer according to the invention makes it possible to advantageously combine performance levels in terms of thickening effect, of clarity and of suspending properties. In other words, it makes it possible to obtain an aqueous formulation having the desired viscosity and comprising a limpid continuous phase and suspended particles distributed homogeneously in the continuous phase.

TABLE 2

| | | 1 | 2 | 3 | 4 | 5 | 6 | 7 | 8 | 9 | 10 | 11 | 12 |
|---|---|---|---|---|---|---|---|---|---|---|---|---|---|
| | | | | | | | Example | | | | | | |
| | | According to the invention | | | | | | | | Comparative | | | |
| Applicative results at 3% (or * at 2.4% and at pH = 5) | Brookfield viscosity (mPa·s) pH = 5 | 13 900 | 13 340 | 12 800 | 10 060 | 8200 | 13 560 | 11 280 | 19 080 | 17 160* | 5920* | 8000* | 2970 |
| | Brookfield viscosity (mPa·s) pH = 6 | 26 300 | 19 600 | 21 800 | 25 690 | 19 400 | 21 700 | 24 190 | 29 800 | NA | NA | NA | 1530 |
| | Brookfield viscosity (mPa·s) pH = 7 | 7000 | 9380 | 12 420 | 10 180 | 11 000 | 9880 | 6600 | 13 840 | NA | NA | NA | 20 100 |
| | Tan (delta) pH = 7 (* at pH = 5) | 0.33 | 0.37 | 0.33 | 0.32 | 0.24 | 0.35 | 0.33 | 0.39 | 0.36* | 1.33* | 0.67* | 1.89 |
| | T at 500 nm (%) pH = 7 (* at pH = 5) | 97 | 96 | 98 | 97 | 92 | 97 | 94 | 98 | 94* | 98* | 94* | 99 |

TABLE 2-continued

| | 1 | 2 | 3 | 4 | 5 | 6 | 7 | 8 | 9 | 10 | 11 | 12 |
|---|---|---|---|---|---|---|---|---|---|---|---|---|
| | | | | | | Example | | | | | | |
| | According to the invention | | | | | | | | | Comparative | | |
| G' (Pa) pH = 7 (* at pH = 5) | 52 | 79 | 95 | 84 | 107 | 86 | 64 | 102 | 71* | 5* | 30* | 31 |
| Elastic strength (dyn/cm²) pH = 7 (* at pH = 5) | | 96 | 95 | 95 | 96 | 96 | NA | 119 | 93* | 0* | 229* | 0 |

The invention claimed is:

1. A copolymer (P1), comprising, in polymerized form:
   (a) an anionic monomer having polymerizable ethylenic unsaturation, comprising acrylic acid, methacrylic acid, an acrylic acid salt, a methacrylic acid salt, or a mixture of two or more of any of these;
   (b) a hydrophobic nonionic monomer having polymerizable ethylenic unsaturation, comprising a $C_1$-$C_8$-alkyl acrylate, $C_1$-$C_8$-alkyl methacrylate, $C_1$-$C_8$-alkyl maleates, $C_1$-$C_8$-alkyl itaconate, $C_1$-$C_8$-alkyl crotonate, $C_1$-$C_8$-alkyl cinnamate, or a mixture of two or more of any of these: and
   (c) a monomer of formula (I)

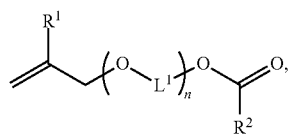

(I)

wherein
$R^1$ is independently H or $CH_3$,
$R^2$ is independently $-C(H)=CH_2$, $-C(CH_3)=CH_2$, $-C(H)=C(H)C(O)OH$, $-C(H)=C(H)CH_3$, $-C(=CH_2)CH_2C(O)OH$, or $-CH_2C(=CH_2)C(O)OH$,
$L^1$ is independently an ethylene, propylene, or butylene group, and
n is independently an integer or decimal in a range of from 3.5 to 30.

2. The copolymer of claim 1, wherein the anionic monomer (a) is an anionic monomer comprising a polymerizable vinyl function and a carboxylic acid function, and comprises the acrylic acid and/or the methacrylic acid and optionally further comprises maleic acid, itaconic acid, crotonic acid, an acrylic acid salt, a methacrylic acid salt, a maleic acid salt, an itaconic acid salt, a crotonic acid salt, and/or cinammic acid salt.

3. The copolymer of claim 1, wherein the hydrophobic nonionic monomer (b) is a hydrophobic nonionic monomer comprising a polymerizable vinyl function, and comprises methyl acrylate, ethyl acrylate, butyl acrylate, 2-ethylhexyl acrylate, methyl methacrylate, ethyl methacrylate, butyl methacrylate, or a mixture thereof.

4. The copolymer of claim 1, wherein the monomer (c) is selected from the group consisting of
   a compound (c1) of formula (I) wherein $R^1$ is H, $R^2$ is $-C(H)=CH_2$, $L^1$ is $CH_2$-$CH_2$, and n is 10;
   a compound (c2) of formula (I) wherein $R^1$ is H, $R^2$ is $-C(CH_3)=CH_2$, $L^1$ is $CH_2$-$CH_2$, and n is 3.5; and
   a compound (c3) of formula (I) wherein $R^1$ is H, $L^1$ is $CH_2$-$CH_2$, $R^2$ is $-C(CH_3)=CH_2$, and n is 10.

5. The copolymer of claim 1, further comprising, in polymerized form:
   (d) a nonionic monomer, different than from the hydrophobic nonionic monomer (b), comprising a polymerizable vinyl function and a hydrocarbon-based chain comprising at least 10 carbon atoms.

6. The copolymer of claim 1, further comprising, in polymerized form:
   (e) an ionic or nonionic monomer, different from the hydrophobic nonionic monomer (b), which is at least one selected from the group consisting of:
   2-acrylamido-2-methylpropane sulfonic acid or a salt thereof;
   a telomer, which is unsaturated, of acrylic acid;
   a monomer of formula (III)

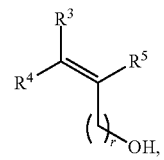

(III)

wherein
$R^3$, $R^4$, and $R^5$ are independently H or $CH_3$, and
r is independently 1, 2, or 3;
a monomer of formula (IV)

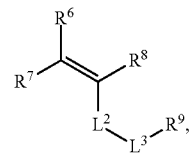

(IV)

wherein
$R^6$, $R^7$, and $R^8$ are independently H or $CH_3$,
$R^9$ is H or $CH_3$,
$L^2$ is independently a direct bond or an O, C(O)O, $CH_2CH_2$, or $CH_2$ group, and
$L^3$ is independently a direct bond or from 1 to 150 alkyleneoxy groups.

7. The copolymer of claim 1 further comprising:
   (f) a further monomer.

8. The copolymer of claim 1, further comprising, in polymerized form, a monomer (g) selected from the group consisting of:
   a compound of formula (VI)

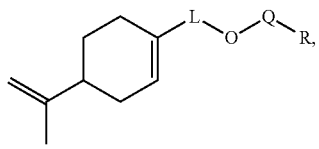

(VI)

wherein
L is CH$_2$, monoalkoxylated CH$_2$, or polyalkoxylated CH$_2$,
Q is a direct or C(O) bond,
R is —C(H)=CH$_2$, —C(CH$_3$)=CH$_2$, —C(H)C(O)OH, —C(H)=C(H)CH$_3$, —C(=CH$_2$)CH$_2$C(O)OH, —CH$_2$C(=CH$_2$)C(O)OH, Q$^3$OQ$^4$OC(O)C(CH$_3$)=CH$_2$, or Q$^3$OQ$^4$OC(O)C(H)=CH$_2$,
Q$^3$ is a divalent residue of an asymmetric diisocyanate compound, and
Q$^4$ is CH$_2$, CH$_2$-CH$_2$, monoalkoxylated CH$_2$, monoalkoxylated CH$_2$-CH$_2$, polyalkoxylated CH$_2$, or polyalkoxylated CH$_2$-CH$_2$;
a compound of formula (VI-A)

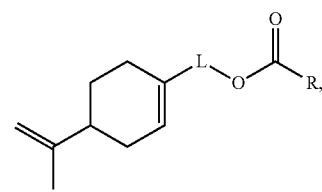

(VI-A)

wherein
L is CH$_2$, monoalkoxylated CH$_2$, or polyalkoxylated CH$_2$,
R is —C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH, Q$^3$OQ$^4$OC(O)C(CH$_3$)=CH$_2$, or Q$^3$OQ$^4$OC(O)C(H)=CH$_2$,
Q$^3$ is a divalent residue of an asymmetric diisocyanate compound, and
Q$^4$ is CH$_2$, CH$_2$-CH$_2$, monoalkoxylated CH$_2$, monoalkoxylated CH$_2$-CH$_2$, polyalkoxylated CH$_2$, or polyalkoxylated CH$_2$-CH$_2$; and
a compound of formula (VI-B)

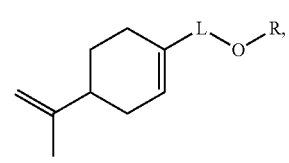

(VI-B)

wherein
L is CH$_2$, monoalkoxylated CH$_2$, or polyalkoxylated CH$_2$,
R is —C(H)=CH$_2$, —C(CH$_3$)=CH$_2$, —C(H)C(O)OH, —C(H)=C(H)CH$_3$, —C C(=CH$_2$)CH$_2$C(O)OH, —CH$_2$C(=CH$_2$)C(O)OH, Q$^3$OQ$^4$OC(O)C(CH$_3$)=CH$_2$, or Q$^3$OQ$^4$OC(O)C(H)=CH$_2$,
Q$^3$ is a divalent residue of an asymmetric diisocyanate compound, and
Q$^4$ is CH$_2$, CH$_2$-CH$_2$, monoalkoxylated CH$_2$, monoalkoxylated CH$_2$-CH$_2$, polyalkoxylated CH$_2$, or polyalkoxylated CH$_2$-CH$_2$.

9. A method for producing the copolymer of claim 1, the method comprising:
producing the copolymer with less than 5 mol relative to the total molar amount of monomers, of at least one monomer of formula (I)

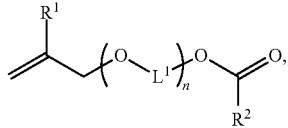

(I)

wherein
R$^1$ is independently H or CH$_3$,
R$^2$ is independently —C(H)=CH$_2$, —C(CH$_3$)=CH$_2$, —C(H)=C(H)C(O)OH, —C(H)=C(H)CH$_3$, —C(=CH$_2$)CH$_2$CH$_2$C(O)OH, or —CH$_2$C(=CH$_2$)C(O)OH,
L$^1$ is independently an ethylene, propylene, or butylene group, and
n is independently an integer or decimal in a range of from 3.5 to 30.

10. A process for producing a copolymer (P1), the process comprising:
polymerizing monomers comprising:
(a) an anionic monomer having polymerizable ethylenic unsaturation comprising acrylic acid, methacrylic acid, an acrylic acid salt, a methacrylic acid salt, or a mixture of two or more of any of these;
(b) a hydrophobic nonionic monomer having polymerizable ethylenic unsaturation, comprising a C$_1$-C$_8$-alkyl acrylate, C$_1$-C$_8$-alkyl methacrylate, C$_1$-C$_8$-alkyl maleates, C$_1$-C$_8$-alkyl itaconate, C$_1$-C$_8$-alkyl crotonate, C$_1$-C$_8$-alkyl cinnamate, or a mixture of two or more of any of these; and
(c) a monomer of formula (I)

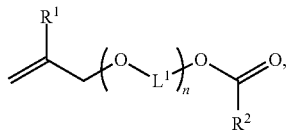

(I)

wherein
R$^1$ is independently H or CH$_3$;
R$^2$ is independently —C(H)=CH$_2$, —C(CH$_3$)=CH$_2$, —C(H)C(O)OH, —C(H)=C(H)CH$_3$, —C(=CH$_2$)CH$_2$C(O)OH, or —CH$_2$C(=CH$_2$)C(O) OH,
L$^1$ is independently an ethylene, propylene, or butylene group, and
n is independently an integer or decimal in a range of from 3.5 to 30.

11. A process for producing a copolymer (P2), the process comprising:
conducting a polymerization reaction with the copolymer (P1) of claim 1, obtained beforehand by a polymerization reaction.

12. A copolymer (P2) produced by the process of claim 11.

13. The copolymer (P2) of claim 12, wherein a 1° copolymer (P1)/2° copolymer (P 1) weight ratio is between 45/55 and 95/5.

14. An aqueous composition comprising:
the copolymer (P2) of claim 12 or
the copolymer (P1).

15. A cosmetic composition, comprising:
the aqueous composition of claim 14;
the copolymer (P1);
the copolymer (P2); or
both of the copolymer (P1) and the copolymer (P2).

16. The composition of claim 15, having a pH in a range of from 3 to 9.

17. A method for producing an aqueous composition or a cosmetic composition, the method comprising:
producing the aqueous composition or the cosmetic composition with the copolymer (P2) of claim 12 and/or the copolymer (P1).

18. The copolymer of claim 1, comprising, in polymerized form, at least 20 mol % of the anionic monomer (a), relative to the total molar amount of monomers.

19. The copolymer of claim 1, comprising, in polymerized form, from 30 to 80 mol % of the hydrophobic nonionic monomer (b), relative to the total molar amount of monomers.

20. The copolymer of claim 1, comprising, in polymerized form, less than 5 mol % of the monomer (c), relative to the total molar amount of monomers.

* * * * *